United States Patent [19]

Ikimi et al.

[11] Patent Number: 5,600,026

[45] Date of Patent: Feb. 4, 1997

[54] PROCESS FOR PRODUCTION OF CRESOLS

[75] Inventors: Kiyoshi Ikimi; Yoichi Ikeda; Akira Murakami; Kazushige Okamoto; Tooru Tokumaru; Motoo Hazama, all of Oita, Japan

[73] Assignee: Sumitomo Chemical Company, Limited, Osaka-fu, Japan

[21] Appl. No.: 393,031

[22] Filed: Feb. 23, 1995

Related U.S. Application Data

[63] Continuation of Ser. No. 144,448, Nov. 2, 1993, abandoned, which is a continuation-in-part of Ser. No. 49,440, Apr. 20, 1993, abandoned.

[30] Foreign Application Priority Data

May 27, 1992 [JP] Japan .................................... 4-134861
Jul. 1, 1992 [JP] Japan .................................... 4-174222

[51] Int. Cl.⁶ .......................... C07C 37/08; C07C 37/06; C07C 37/68
[52] U.S. Cl. .......................... 568/798; 568/754; 568/799
[58] Field of Search .................................... 568/754, 798, 568/799

[56] References Cited

U.S. PATENT DOCUMENTS

| 2,728,797 | 12/1955 | Filar . |
| 4,431,849 | 2/1984 | Colvin .................................... 568/799 |
| 5,166,451 | 11/1992 | Takeshita et al. . |

FOREIGN PATENT DOCUMENTS

| 1803036 | 8/1969 | Germany . |
| 2650416 | 5/1977 | Germany . |
| 51-25011 | 7/1976 | Japan . |
| 51-46094 | 12/1976 | Japan . |
| 52-12183 | 4/1977 | Japan . |
| 52-57130 | 5/1977 | Japan . |
| 59-8246 | 2/1984 | Japan . |
| 60-54357 | 3/1985 | Japan . |
| 62-34755 | 7/1987 | Japan . |
| 63-35558 | 2/1988 | Japan . |
| 1-49248 | 10/1989 | Japan . |

OTHER PUBLICATIONS

F. Katashi et al., *Chemical Abstracts*, vol. 88, No. 25, Jun. 1978, p. 722, col. 1, Abstract No. 190380.

*Primary Examiner*—Alan Siegel
*Attorney, Agent, or Firm*—Birch, Stewart, Kolasch & Birch, LLP

[57] ABSTRACT

There is disclosed a process for the production of cresols, including the steps of: (a) conducting oxygenation of cymene with oxygen gas or an oxygen-containing gas, thereby obtaining a solution of oxygenation products containing tertiary and primary hydroperoxides of cymene; (b) reacting the solution of oxygenation products obtained in the step (a) with an organic quaternary ammonium salt and an alkali, or with an organic quaternary ammonium hydroxide, thereby decreasing the content of primary hydroperoxide; (c) subjecting the reaction mixture in the step (b) to decomposition in the presence of a catalyst; and (d) subjecting the decomposition mixture in the step (c) to hydrogenation, thereby obtaining the desired cresols.

22 Claims, No Drawings

PROCESS FOR PRODUCTION OF CRESOLS

CROSS REFERENCE

This application is a continuation of application Ser. No. 08/144,448 filed on Nov. 2, 1993, now abandoned which is application Ser. No. 08/045440, filed Apr. 20, 1993 now abandoned.

FIELD OF THE INVENTION

The present invention relates to a process for the production of cresols.

BACKGROUND OF THE INVENTION

As a process for cresol production, there has been widely known a process in which cymene is oxygenated with oxygen gas and the resulting tertiary hydroperoxide of cymene is then decomposed into the desired cresols and acetone.

In this process, however, a primary hydroperoxide of cymene with an oxygenated methyl group is formed as a by-product in the oxygenation, together with the above tertiary hydroperoxide. The primary hydroperoxide is converted into isopropylphenol and formaldehyde through its decomposition. This formaldehyde may be condensed with the resulting cresols to form a resin, which will cause a decrease in the yield of cresols in this process.

To solve this problem, a process has been proposed, in which the decomposition of the primary hydroperoxide is stopped halfway to suppress the formation of formaldehyde, so that a yield decrease arising from this by-product can be prevented, and the remaining primary hydroperoxide is then hydrogenated into an alkylbenzene (see, e.g., JP-A 52-57130, JP-B 59-8246, JP-B 1-49248).

In this process, however, a portion of the primary hydroperoxide still decomposes. Therefore, there will inevitably occur to a certain degree the side reaction between formaldehyde as the by-product and cresols as the major product, so that a loss of cresol yield will accompany the process. This process is not satisfactory with respect to the yield of cresols.

For the purpose of preventing the formation of formaldehyde, a process has been proposed, in which a mixture of the tertiary and primary hydroperoxides obtained by the oxygenation is reacted with an alkali and an organic quaternary ammonium salt to reduce the content of primary hydroperoxide (see, e.g., JP-A 63-35552). This process involves no formation of formaldehyde as a by-product in the production of cresols, so that any decrease in the yield of cresols arising from The formaldehyde formation can be prevented; however, the primary hydroperoxide is not effectively utilized in this process, and it cannot always be said that this process is satisfactory from the viewpoint of an improvement in the yield of cresols.

SUMMARY OF THE INVENTION

Under these circumstances, the present inventors have intensively studied a production process for cresols. As the result, they have found a novel process through a series of steps comprising: reacting, in advance of decomposition, with an organic quaternary ammonium salt and an alkali, or with an organic quaternary ammonium hydroxide, a solution of oxygenation products containing the tertiary and primary hydroperoxides of cymene, which has been obtained by oxygenation of cymene with oxygen gas or an oxygen-containing gas, so that the content of primary hydroperoxide is decreased; subjecting the reaction mixture to decomposition; and subjecting the decomposition mixture to hydrogenation, thereby obtaining cresols with high yield.

This process makes it possible to prevent any decrease in the yield of cresols arising from the formation of formaldehyde by decomposition of the primary hydroperoxide which is usually seen in any conventional process as described above, and also makes it possible to selectively recover the decomposition products of the primary hydroperoxide and other by-products in the form of cymene as the raw material, thereby attaining an improvement in the yield of cresols.

That is, the present invention provides a process for the production of cresols, comprising the steps of:

(a) conducting oxygenation of cymene with oxygen gas or an oxygen-containing gas, thereby obtaining a solution of oxygenation products containing tertiary and primary hydroperoxides of cymene; (b) reacting the solution of oxygenation products obtained in the step (a) with an organic quaternary ammonium salt and an alkali, or with an organic quaternary ammonium hydroxide, thereby decreasing the content of primary hydroperoxide; (c) subjecting the reaction mixture in the step (b) to decomposition in the presence of a catalyst; and (d) subjecting the decomposition mixture in the step (c) to hydrogenation, thereby obtaining the desired cresols.

DETAILED DESCRIPTION OF THE INVENTION

The following will describe the step of conducting the oxygenation of cymene with oxygen gas or an oxygen-containing gas no obtain a solution of oxygenation produces containing tertiary and primary hydroperoxides of cymene.

The raw material, cymene, used in this step may be in various forms such as o-cymene, m-cymene and p-cymene. The compounds of these forms can be used solely or in combination with each other at any proportion.

This seep can be performed by ordinary oxygenation in liquid phase, and usually attained by bringing cymene in contact with oxygen gas or an oxygen-containing gas such as air.

The oxygenation is usually conducted under normal pressure or under pressure. The pressure of oxygen gas or an oxygen-containing gas is usually in the range of from 0 to 20 $kg/cm^2$ as a gauge pressure.

In this step, an alkali may be allowed no coexist in the reaction system, examples of which are carbonates of alkali metals, such as sodium carbonate and potassium carbonate; hydroxides of alkaline earth metals, such as magnesium hydroxide and calcium hydroxide; carbonates of alkaline earth metals, such as calcium carbonate; amines such as pyridine, piperidine and triethylamine; and ammonia. These alkalis may be used in the form of a solution, if possible.

In this step, an initiator may be added co the reaction system, examples of which are azo compounds such as 2,2'-azobisisobutyronitrile, and peroxides such as benzoyl peroxide and cymene hydroperoxide. The amount of initiator to be used is usually in the range of from 0.01% to 5% by weight, based on the weight of cymene.

The reaction temperature is usually in the range of from 30° to 200° C., preferably from 80° to 150° C.

The ratio of formed primary hydroperoxide to formed tertiary hydroperoxide is usually in the range of from 5-30/95-70 (primary/tertiary; the sum total of both is 100).

After completion of the reaction, a solution of oxygenation products is obtained, which may be further subjected, if necessary, to an ordinary post-treatment such as fractionation with a separatory funnel or filtration. This solution of oxygenation products can be used in the subsequent step without undergoing a particular post-treatment; in case where no alkali is used in this step, however, the resulting solution of oxygenation products may be washed, before its use in the subsequent step, with an aqueous solution of alkali substances such as hydroxides of alkali metals, carbonates of alkali metals, hydroxides of alkaline earth metals or carbonates of alkaline earth metals.

The following will describe the step of reacting the solution of oxygenation products obtained in the foregoing step with an organic quaternary ammonium salt and an alkali, or with an organic quaternary ammonium hydroxide, thereby decreasing the content of primary hydroperoxide.

Examples of the organic quaternary ammonium salt which can be used in this reaction are a compound of the general formula:

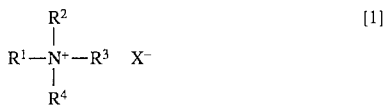
[1]

wherein $R^1$ and $R^2$ are independently a $C_1$–$C_{24}$ alkyl group or an aralkyl group, both of which are optionally substituted with at least one substituent; $R^3$ and $R^4$ are independently a $C_1$–$C_{10}$ alkyl group; and X is an anion reside; and a compound of the general formula:

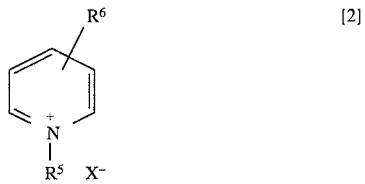
[2]

wherein $R^5$ is an optionally substituted $C_1$–$C_{24}$ alkyl group; $R^6$ is a hydrogen atom or a $C_1$–$C_2$ alkyl group; and X is the same as defined above.

In both compounds as shown above, examples of the anion residue are halogen atoms such as chlorine, bromine and iodine; and acid residues such as $H_2PO_4$, $CH_3COO$, $CH_3OSO_3$, $C_2H_5OSO_3$, $ClO_4$ and $HSO_4$.

As the optionally substituted aralkyl group in the compound [1], there can be exemplified benzyl, 1-phenethyl and 2-phenethyl, all of which may be substituted in any way.

Typical examples of the compounds [1] and [2] are tetramethylammonium chloride, tetraethylammonium chloride, tetra-n-propylammonium chloride, tetra-n-butylammonium chloride, benzyltrimethylammonium chloride, benzyltriethylammonium chloride, stearyltrimethylammonium chloride, trimethyloctadecylammonium chloride, lauryltrimethylammonium chloride, trimethylhexadecylammonium chloride, distearyldimethylammonium chloride, dicetyldimethylammonium chloride, tricaprylmethylammonium chloride, o-, m- and p-methoxybenzyltriethylammonium chlorides, o-, m- and p-phenoxybenzyltriethylammonium chlorides, trimethyldodecylammonium chloride, trimethyldecylammonium chloride, triocrioctylmethylammonium chloride, N-butylpyridinium chloride, N-laurylpyridinium chloride, N-laurylpicolinium chloride, triethylpropylammonium chloride, diethylpropylbenzylammonium chloride, o-, m- and p-chlorobenzyltriethylammonium chlorides, methylethylpropylbenzylammonium chloride, diethylbutylbenzylammonium chloride, methyldiethylbenzylammonium chloride, dimethylethylbenzylammonium chloride, tripropylbenzylammonium chloride, ethyldipropylbenzylammonium chloride, diethyldibenzylammonium chloride, dimethyllaurylbenzylammonium chloride, dimethylstearylbenzylammonium chloride, dimethyloctylbenzylammonium chloride, dimethylmyristylbenzylammoium chloride, as well as bromides, iodides, perchlorates, dihydrogenphosphates, hydrogensulfates, methylsulfates and ethylsulfates corresponding to these chlorides. These compounds can be used solely or in admixture with each other. The amount of these compound to be used is usually in the range of from 0.001 to 1 mole, preferably from 0.001 to 0.5 moles, per mole of the primary hydroperoxide.

Examples of the alkali which can be used together with the organic quaternary ammonium salt are hydroxides of alkali metals and hydroxides of alkaline earth metals, such as sodium hydroxide, potassium hydroxide, lithium hydroxide, calcium hydroxide, barium hydroxide, magnesium hydroxide and strontium hydroxide. The amount of alkali to be used is usually in the range of from 0.1 to 20 moles, preferably from 0.5 to 10 moles, per mole of the primary hydroperoxide.

In case where an organic quaternary ammonium hydroxide is used in the above reaction, it is possible to use a compound of the general formula:

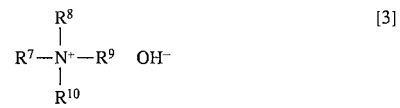
[3]

wherein $R^7$ and $R^8$ are independently a $C_1$–$C_{24}$ alkyl group or an aralkyl group, both of which are optionally substituted with at least one substituent; $R^9$ and $R^{10}$ are independently a $C_1$–$C_{10}$ alkyl group; or a compound of the general formula:

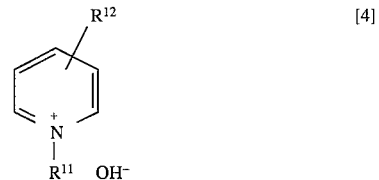
[4]

wherein $R^{11}$ is an optionally substituted $C_1$–$C_{24}$ alkyl group; $R^{12}$ is a hydrogen atom or a $C_1$–$C_2$ alkyl group.

As the optionally substituted aralkyl group in the compound [3], there can be exemplified benzyl, 1-phenethyl and 2-phenethyl, all of which may be substituted in any way.

Typical examples of the compounds [3] and [4] are tetramethylammonium hydroxide, tetraethylammonium hydroxide, tetra-n-propylammonium hydroxide, tetra-n-butylammonium hydroxide, benzyltrimethylammonium hydroxide, benzyltriethylammonium hydroxide, stearyltrimethylammonium hydroxide, trimethyloctadecylammonium hydroxide, lauryltrimethylammonium hydroxide, trimethylhexadecylammonium hydroxide, distearyldimethylammonium hydroxide, dicetyldimethylammonium hydroxide, tricaprylmethylammonium hydroxide, o-, m- and p-methoxybenzyltriethylammonium hydroxides, o-, m- and p-phenoxybenzyltriethylammonium hydroxides, trimethyldodecylammonium hydroxide, trimethyldecylammonium hydroxide, trioctylmethylammonium hydroxide, N-butylpyridinium hydroxide, N-laurylpyridinium hydroxide, N-laurylpicolinium hydroxide, triethylpropylammonium hydroxide, diethylpropylbenzylammonium hydroxide, o-, m- and p-chlorobenzyltriethylammonium hydroxides, methylethylpropylbenzylammonium hydroxide, diethylbutylbenzylammonium hydroxide, methyldiethylbenzylammonium hydroxide, dimethylethylbenzylammonium hydroxide, tripropylbenzylammonium hydroxide, ethyldipropylbenzylammonium hydroxide, diethyldibenzylammonium hydroxide, dimethyllaurylbenzylammonium hydroxide, dimethylstearylbenzylammonium hydroxide, dimethyloctylbenzylammonium hydroxide and dimethylmyristylbenzylammoium hydroxide. These hydroxides can be used solely or in admixture with each other. The amount of these hydroxides to be used is usually in the range of from 0.001 to 5 moles, per mole of the primary hydroperoxide.

In case where an organic quaternary ammonium hydroxide is used, it is preferred to combine an alkali therewith, because the amount of organic quaternary ammonium hydroxide to be used can be decreased. The amount of organic quaternary ammonium hydroxide to be used in this case is usually in the range of from 0.001 to 1 mole, preferably 0.001 to 0.5 moles, per mole of the primary hydroperoxide. The amount of organic quaternary ammonium hydroxide to be used with no alkali is usually in the range of from 0.1 to 5 moles, preferably 0.3 to 3 moles, per mole of the primary hydroperoxide.

Examples of the alkali which can be used together with the organic quaternary ammonium hydroxide are hydroxides of alkali metals and hydroxides of alkaline earth metals, such as sodium hydroxide, potassium hydroxide, lithium hydroxide, calcium hydroxide, barium hydroxide, magnesium hydroxide and strontium hydroxide. The amount of alkali to be used is usually in the range of from 0.1 to 20 moles, preferably from 0.5 to 10 moles, per mole of the primary hydroperoxide.

The reaction in this step is usually conducted in the presence of a polar solvent such as water, methanol or ethanol. Preferably used is water.

The reaction temperature is usually in the range of from 30° C, to 150° C., preferably from 70° C. to 110° C.

By this selective decomposition, the primary hydroperoxide is selectively decomposed, so that formaldehyde cannot be formed as a by-product in the subsequent decomposition step for obtaining the desired cresols. Accordingly, there is no possibility that the yield of cresols may be decreased by the side reaction between the resulting cresols and the formaldehyde. Further, by the additional hydrogenation of the reaction mixture after the decomposition of the tertiary hydroperoxide into the cresols, the decomposition products from the primary hydroperoxide and other by-products are converted into the raw material cymene which will be recycled, resulting in an increase in the yield of cresols from the consumed cymene.

While the decomposition reaction is selective, the tertiary hydroperoxide can also be reacted, together with the primary hydroperoxide. The reaction rate of the tertiary hydroperoxide is considerably lower than that of the primary hydroperoxide, and the decomposition products from the tertiary hydroperoxide can be recovered in the form of cymene by hydrogenation after the decomposition of the tertiary hydroperoxide into cresols; therefore, the final yield of cresols from consumed cymene becomes higher than that attained by any conventional process. It is, however, disadvantageous from an economical point of view that the tertiary hydroperoxide is decomposed to a degree than required. It is usually advantageous from an economical point of view, i.e., the yield of cresols through one pass and the energy efficiency in the process, that the decomposition is conducted so that the weight ratio of primary hydroperoxide to tertiary hydroperoxide is usually decreased to not greater than 1/25 (w/w), preferably not greater than 1/50 (w/w), more preferably not greater than 1/100 (w/w), which makes it possible to decrease the formation of by-products responsible for any yield decrease in the subsequent step, and that the degree of conversion of tertiary hydroperoxide as the precursor of cresols is suppressed to become 20% or less, preferably 10% or less, more preferably 5% or less.

These results of decomposition can be attained by adjusting the concentration of alkali, the amount of organic quaternary ammonium salt or hydroxide to be used, and the reaction temperature, to the above prescribed values.

In this step, the reaction mixture may be subjected to an analysis such as liquid chromatography to check the weight ratio of primary hydroperoxide to tertiary hydroperoxide, which also makes it possible to determine the end point of the reaction.

After completion of the reaction, for example, the reaction mixture may be allowed to stand and subjected to fractionation with a separatory funnel, followed by washing with water, before its use in the subsequent step.

The following will describe the step of subjecting the reaction mixture obtained in the foregoing step to decomposition in the presence of a catalyst.

Examples of the catalyst which can be used in this step are acidic catalysts, sulfur and Burman catalysts. Specific examples of the acidic catalyst are inorganic acids such as sulfuric acid, hydrochloric acid, perchloric acid, $SO_2$ and $SO_3$; organic acids such as benzenesulfonic acid, p-toluenesulfonic acid, cresolsulfonic acid and chloroacetic acid; solid acids such as silica-alumina, alumina and acidic ion exchange resin; heteropolyacids such as tungstosilicic acid, tungstophosphoric acid and molybdophosphoric acid. The Burmah catalyst refers to a catalyst carrying a metal complex of the general formula:

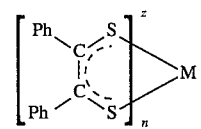

[5]

wherein M is Ni, Pd or Fe(II); Ph is a phenyl group optionally substituted with at least one substituent; n is an integer of 1, 2 or 3; z is a formal charge of the complex, selected from 0, −1 and −2. Examples of the Burmah catalyst are bis(dithiobenzil)nickel, bis(dithiobenzil)palladium and bis(dithiobenzil)iron(II). Preferred catalysts are sulfuric acid and cresolsulfonic acid. The amount of catalyst to be used, although it can be determined depending upon the kind of that catalyst, is usually in the range of from about 0.0001% to 1% by weight, based on the weight of the reaction mixture to be treated.

The reaction temperature is usually in the range of from 30° to 150° C.

In this step, the mixture thus treated may be subjected to an analysis such as liquid chromatography to check the degree of decomposition of hydroperoxides.

After completion of the reaction, the reaction mixture can be used in the subsequent seep without under-going a particular post-treatment, or if necessary, after subjected to a post-treatment such as filtration and neutralization. Alternatively, the reaction mixture can also be used in the subsequent step after the removal of acetone produced.

The following will describe the step of subjecting the decomposition mixture obtained in the foregoing seep to hydrogenation.

This step can be performed by ordinary catalytic hydrogenation, and usually attained by introducing hydrogen gas in the reaction system under normal pressure or under pressure in the presence of a catalyst. The pressure of hydrogen gas is usually in the range of from 0 to 100 kg/cm² as a gauge pressure.

Examples of the catalyst which can be used in this step are those composed of a metal such as Pd, Cr, Cu, Pt, Ni, Ru, Rh or Re. These catalysts can also be used in a supported form on a carrier such as active carbon, titania, zirconia, silica-magnesia, alumina-magnesia, alumina or acidic ion exchange resin. Preferred are those composed of Pd or Cu—Cr. More preferred are Pd/C, Pd/alumina, Pd/TiO₂, Cu—Cr/C, Cu—Cr/TiO₂ and Pd/acidic ion exchange resin. The amount of catalyst to be used is usually in the range of from 0.001% to 20% by weight, based on the weight of the decomposition mixture to be treated.

In this step, any other catalyst may be allowed to coexist in the reaction system, if necessary. Examples of such a catalyst are. the same catalysts as used in the decomposition step. The decompostion mixture may be used as it is, without undergoing the removal of the catalyst used in the decomposition step.

The reaction temperature is usually in the range of from 0° to 250° C., preferably from 20° to 250° C.

After completion of the reaction, the removal of the catalyst by filtration gives cresols, cymene and acetone, which can be separated and purified, if necessary, by neutralization and then distillation.

The by-products formed by the selective decomposition of the primary hydroperoxide in the foregoing step can be converted into cymene and then recovered, together with the unreacted portion of cymene, both being recycled as the raw material in the process of the present invention.

The process of the present invention comprising the aforesaid steps is quite different from any conventional process in that any decrease in the yield of cresols arising from their reaction with the by-product formaldehyde can be prevented and the by-products formed by oxygenation of cymene can effectively be recovered in the form of cymene, thereby attaining an improvement in the yield of cresols from consumed cymene, as compared with that obtained by any conventional process.

The process of the present invention can be performed either by a batch or a continuous method.

According to the process of the present invention, cresols can be obtained in high yield by conducting oxygenation of cymene with oxygen gas or an oxygen-containing gas, followed by treatment with an organic quaternary ammonium salt and an alkali, or with an organic quaternary ammonium hydroxide, thereby decreasing the content of primary hydroperoxide, and further by subjecting the reaction mixture to decomposition and then hydrogenation, thereby preventing the side reaction responsible for any yield decrease and effectively recovering the by-products in the form of cymene. The process of the present invention has an additional advantage that the resulting cresols can readily be isolated from the by-products.

The present invention will be further illustrated by way of the following examples which are not to be construed to limit the scope thereof.

The following abbreviated names are used in the Examples with reference to the compounds of the respective structures as shown below.

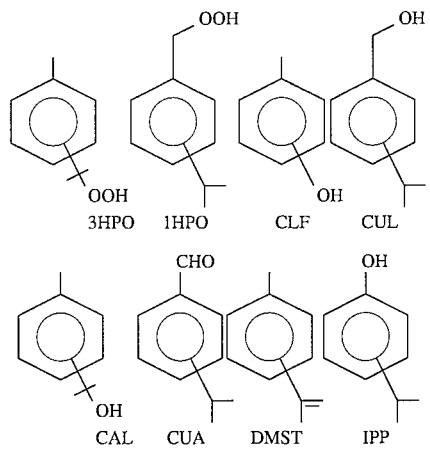

EXAMPLE 1

I. In a reaction vessel equipped with a stirrer, an air-blowing tube, a thermometer and a condenser, placed is raw material cymene (5045 parts by weight; composition: cymene, 98.3%; 3HPO, 1.10%; 1HPO, 0.032%; CAL, 0.122%; CUL, 0.007%; CUA, 0.0540%; CLF, 0.007%) containing cymene hydroperoxide (1.13%) as a reaction initiator. The reaction is conducted, while blowing air thereinto, at 120° C. under normal pressure for 6 hours. After completion of the reaction, 5116 parts by weight of a solution of oxygenation products (composition: cymene, 86.2%; 3HPO, 9.28%; 1HPO, 1.68%; CAL, 0.620%; CUL, 0.073%; CUA, 0.125%; CLF, 0.006%) is obtained.

II. The solution of oxygenation products (500 parts by weight) obtained in Sec. I. of this Example is placed in a reaction vessel, to which benzyltriethylammonium chloride (0.507 parts by weight) and 8% aqueous sodium hydroxide (49.5 parts by weight) are added, and the mixture is stirred at 80° C. for 2.5 hours. The mixture is allowed to stand and the water phase is removed therefrom with a separatory funnel to give 498 parts by weight of the organic phase (composition: cymene, 86.3%; 3HPO, 9.22%; 1HPO, 0.005%; CAL, 0.953%; CUL, 0.114%; CUA, 1.69%; CLF, 0.001%). The weight ratio of 1HPO to 3HPO in the organic phase is 1/1844, and the degree of conversion is 99.7% for 1HPO and 0.972% for 3HPO, respectively.

To a reaction vessel charged with one portion of the resulting organic phase (488 parts by weight), added is water (50.0 parts by weight.), and the mixture is stirred for washing at 80° C. for 1 hour. Then, the mixture is allowed to stand and the water phase is removed therefrom with a separatory funnel to give 487 parts by weight of the washed organic phase (composition: cymene, 86.4%; 3HPO, 9.36%; 1HPO, 0.007%; CAL, 0.984%; CUL, 0.130%; CUA, 1.67%; CLF, 0.001%).

One portion of the resulting washed organic phase (477 parts by weight) is condensed at 70° C. under reduced pressure (10 to 20 mmHg) to recover 391 parts by weight of cymene (cymene content, 98.7%) as a distillate and to give 83.9 parts by weight of condensed oil (composition: cymene, 30.5%; 3HPO, 51.9%; 1HPO, 0.0710%; CAL, 5.46%; CUL, 0.620%; CUA, 9.17%; CLF, not found) as a bottom residue.

III. The concentrated oil (20.0 parts by weight) obtained in Sec. II of this Example is added to a mixture of sulfuric acid (0.00803 parts by weight) and acetone (2.01 parts by weight) under reflux with stirring. After completion of the addition, the mixture is maintained at 65° C. for 15 minutes to give 21.7 parts by weight of the decomposition mixture (composition: cymene, 28.4%; 3HPO, not found; 1HPO, not found; CAL, 0.417%; CUL, 1.57%; CUA, 7.31%; CLF, 30.0%; DMST, 3.00%; others, 29.3%). The degree of conversion of 3HPO is 100% and the yield of CLF is 96.6% (from 3HPO before the acid decomposition). The total yield of cresol from the oxygenation step to this step is 58.8%.

IV. In an autoclave made of stainless steel, placed are the decomposition mixture (15.0 parts by weight) obtained in Sec. III. of this Example, 5% palladium-titania catalyst (0.300 parts by weight) and acidic ion exchange resin (Rohm & Haas Co.; trade name, Amberlyst 15; 0.294 parts by weight). The hydrogenation is conducted, while introducing hydrogen gas thereinto under a hydrogen gauge pressure of 5 kg/cm$^2$, at 40° C. for 2 hours and then at 75° C. for 1 hour. After completion of the reaction, the catalyst is removed by filtration, and. the reaction mixture is neutralized by addition of aqueous sodium hydroxide until the water phase has pH 7. The reaction mixture is allowed to stand and the water phase is removed therefrom with a separatory funnel to give 15.0 parts by weight of the reaction mixture (composition: cymene, 42.8%; 3HPO, not found; 1HPO, not found; CAL, 0.0730%; CUL, 0.161%; CUA, not found; CLF, 30.7%; DMST, 0.363%; others, 25.9%). The total yield of cresol is 78.2% (from consumed cymene).

The degree of conversion of by-products (CAL+DMST+CUA+CUL) in this reduction step is 95.0%, the yield of cymene is 126.1% (from by-products (CAL+DMST+CUA+CUL) before the hydrogenation), and the recovery-of cresol is 102.3% (to the amount of cresol before the hydrogenation).

EXAMPLES 2–10

The oxygenation mixture obtained in Sec. I of Example 1 is used for the treatment of a hydroperoxide mixture with an organic quaternary ammonium salt or hydroxide in the same manner as described in Sec. II of Example 1, except for the conditions shown in Table 1. The results are shown in Table 1.

The reaction mixture obtained in the foregoing step is washed with water and concentrated, after which the subsequent steps are conducted in the same manner as described in Secs. III-IV of Example 1, thereby obtaining the desired cresols and cymene with high yield.

EXAMPLE 11

The oxygenated oil (250 parts by weight; composition: cymene, 85.2%; 3HPO, 9.84%; 1HPO, 1.58%; CAL, 0.873%; CUL, 0.142%; CUA, 0.153%; CLF, 0.015%) obtained in Sec. I of Example 1 is stirred together with 4% aqueous sodium hydroxide (25.0 parts by weight) under an atmosphere of nitrogen at 70° C. for 0.25 hours to give 250 parts by weight of neutralized oil (composition: cymene, 85.2%; 3HPO, 9.77%; 1HPO, 1.39%; CAL, 0.909%; CUL, 0.220%; CUA, 0.233%; CLF, 0.003%).

This neutralized oil (200 parts by weight) is placed in a reaction vessel, to which 8% aqueous sodium hydroxide (19.9 parts by weight) and benzyltriethyl ammonium chloride (0.599 parts by weight) are added, and the mixture is stirred under an atmosphere of nitrogen at 70° C. for 0.25 hours. The reaction mixture is allowed to stand and the water phase is removed with a separatory funnel to give 200 parts by weight of organic phase (composition: cymene, 85.2%; 3HPO, 9.57%; 1HPO, 0.052%; CAL, 1.06%; CUL, 0.317%; CUA, 1.76%; CLF, 0.003%).

The weight ratio of 1HPO to 3HPO in the organic phase is 1/185, and the degree of conversion is 96.3% for 1HPO and 2.03% for 3HPO, respectively.

EXAMPLES 12–21

The decomposition mixture obtained in Secs. I-III of Example 1 is subjected to hydrogenation in the same manner as described in Sec. IV of Example 1, except for the conditions shown in Table 2. The results are shown in Table 2.

TABLE 1

| Example No. | Organic quaternary ammonium salt or hydroxide | | Mole ratio of alkali (to 1HPO) | Reaction time (hr) | 1HPO conv. (%) | 3HPO conv. (%) | 1HPO/3HPO in oil phase after reaction (weight ratio) |
|---|---|---|---|---|---|---|---|
| | Kind | Mole ratio (to 1HPO) | | | | | |
| 2 | Benzyltriethyl-ammonium hydroxide | 0.039 | 1.66 | 2.0 | 98.9 | 1.6 | 1/494 |
| 3 | Benzyltriethyl-ammonium hydroxide | 0.49 | 2.08 | 0.17 | 100 | 1.0 | — |
| 4 | Lauryltrimethyl-ammonium chloride | 0.042 | 2.10 | 2.0 | 99.2 | 0.3 | 1/688 |
| 5 | Cetyltrimethyl-ammonium chloride | 0.040 | 2.50 | 2.0 | 99.4 | 1.0 | 1/911 |
| 6 | Stearyltrimethyl-ammonium chloride | 0.031 | 2.10 | 2.0 | 99.3 | 2.2 | 1/772 |
| 7 | Benzyltriethyl-ammonium chloride | 0.11 | 2.52 | 1.33 | 95.3 | 2.1 | 1/115 |
| 8 | Lauryltrimethyl-ammonium chloride | 0.11 | 2.10 | 1.17 | 95.6 | 1.6 | 1/124 |
| 9 | Benzyltriethyl-ammonium hydroxide | 1.1 | 0 | 2.0 | 100 | 2.0 | — |
| 10 | Tetramethyl-ammonium hydroxide | 2.6 | 0 | 2.0 | 100 | 0 | — |

TABLE 2

| Example No. | Catalyst Kind | Catalyst Amount (based on decomp. mixture) | Acid additive Kind | Acid additive Amount (based on decomp. mixture) | Temp. (°C.) Time (hr) | [A]*1 conv. (%) | CYM*2 yield (%) | CLF*3 reco. (%) | Other conds. |
|---|---|---|---|---|---|---|---|---|---|
| 12 | 5% Pd/TiO$_2$ | 1 wt % | Amberlyst 15 | 1 wt % | $\frac{40}{1} + \frac{75}{1}$ | 96.7 | 126.8 | 101.4 | |
| 13 | 5% Pd/TiO$_2$ | 1 wt % | Amberlyst 15 | 2.5 wt % | $\frac{40}{1} + \frac{75}{1}$ | 82.7 | 121.8 | 102.6 | *4 |
| 14 | 5% Pd/TiO$_2$ | 1 wt % | 98% H$_2$SO$_4$ | 0.08 wt % | $\frac{40}{1} + \frac{75}{1}$ | 52.6 | 114.8 | 100.5 | |
| 15 | 5% Pd/TiO$_2$ | 1 wt % | 98% H$_2$SO$_4$ | 0.2 wt % | $\frac{40}{1} + \frac{75}{1}$ | 75.8 | 142.5 | 101.3 | |
| 16 | 5% Pd/TiO$_2$ | 1 wt % | Tungstosilicic acid | 0.5 wt % | $\frac{40}{1} + \frac{75}{1}$ | 83.5 | 149.7 | 100.4 | |
| 17 | 5% Pd/TiO$_2$ | 1 wt % | Tungstophosphoric acid | 0.5 wt % | $\frac{40}{1} + \frac{75}{1}$ | 62.4 | 124.0 | 98.3 | |
| 18 | 5% Pd/Al$_2$O$_3$ | 1 wt % | Amberlyst 15 | 2.5 wt % | $\frac{40}{1} + \frac{75}{1}$ | 94.9 | 168.7 | 102.1 | |
| 19 | 5% Pd/TiO$_2$ | 1 wt % | None | — | $\frac{40}{2}$ | 86.2 | 103.4 | 99.7 | |
| 20 | 5% Pd/TiO$_2$ | 1 wt % | None | — | $\frac{40}{1} + \frac{75}{1}$ | 78.5 | 104.2 | 96.8 | |
| 21 | 2% Pd/IER*5 | 2.5 wt % | None | — | $\frac{40}{1} + \frac{75}{1}$ | 47.6 | 110.3 | 105.1 | |

*1Total conversion of by-products (CAL, DMST, CUA and CUL) in the hydrogenation. [A] = CAL + DMST + CUA + CUL $$[A]\text{conv.} = \frac{\text{amount of [A] before hydrogenation} - \text{amount of [A] after hydrogenation}}{\text{amount of [A] before hydrogenation}} \times 100$$

*2Yield of CYM in the hydrogenation.

$$\text{CYM yield} = \frac{\text{mole of CYM before hydrogenation} - \text{mole of CYM after hydrogenation}}{\text{mole of [A] before hydrogenation}} \times 100$$

*3Recovery of CLF in the hydrogenation.

$$\text{CLF reco.} = \frac{\text{amount of CLF after hydrogenation}}{\text{amount of CLF before hydrogenation}} \times 100$$

*4The decomposition mixture is subjected to neutralization before hydrogenation.
*5Acidic ion exchange resin.

What is claimed is:

1. A process for the production of cresols, comprising the steps of:
    (a) oxygenating cymene with oxygen gas or an oxygen-containing gas in the absence of an alkali, to thereby obtain a solution of oxygenation products containing tertiary and primary hydroperoxides of cymene;
    (b) carrying out a selective decomposition reaction on the oxygenation products obtained in the step (a) under an atmosphere of nitrogen with either:
        (i) an organic quaternary ammonium salt and an alkali, or
        (ii) an organic quaternary ammonium hydroxide, in the presence or absence of alkali
    to thereby selectively decrease said primary hydroperoxides in the solution;
    (c) subjecting the resultant solution from step (b) to decomposition in the presence of an acidic catalyst, or sulfur or a Burmah catalyst; and
    (d) subjecting the resultant solution from step (c) to hydrogenation, subsequently separating and recovering the desired cresols.

2. A process according to claim 1, wherein the reaction in the step (b) is conducted so that the weight ratio of remaining primary hydroperoxide to tertiary hydroperoxide is decreased to not greater than 1/25 (w/w).

3. A process according to claim 2, wherein a degree of conversion of tertiary hydroperoxide in the step (b) is 20% or less.

4. A process according to claim 1, wherein the reaction in the step (b) is conducted with the organic quaternary ammonium salt and the alkali.

5. A process according to claim 2, wherein the reaction in the step (b) is conducted with said organic quaternary salt and said alkali.

6. A process according to claim 3, wherein the reaction in the step (b) is conducted with said organic quaternary ammonium salt and said alkali.

7. A process according to claim 1, wherein the reaction in the step (b) is conducted with said organic quaternary ammonium hydroxide and said alkali.

8. A process according to claim 2, wherein the reaction in the step (b) is conducted with said organic quaternary ammonium hydroxide and said alkali.

9. A process according to claim 3, wherein the reaction in the step (b) is conducted with said organic quaternary ammonium hydroxide and said alkali.

10. A process according to claim 1, wherein the hydrogenation in the step (d) is conducted with a Pd catalyst or a Cu—Cr catalyst.

11. A process according to claim 2, wherein the hydrogenation in the step (d) is conducted with a Pd catalyst or a Cu—Cr catalyst.

12. A process according to claim 3, wherein the hydrogenation in the step (d) is conducted with a Pd catalyst or a Cu—Cr catalyst.

13. A process according to claim 4, wherein the hydrogenation in the step (d) is conducted with a Pd catalyst or a Cu—Cr catalyst.

14. A process according to claim 5, wherein the hydrogenation in the step (d) is conducted with a Pd catalyst or a Cu—Cr catalyst.

15. A process according to claim 6, wherein the hydrogenation in the step (d) is conducted with a Pd catalyst or a Cu—Cr catalyst.

16. A process according to claim 7, wherein the hydrogenation in the step (d) is conducted with a Pd catalyst or a Cu—Cr catalyst.

17. A process according to claim 8, wherein the hydrogenation in the step (d) is conducted with a Pd catalyst or a Cu—Cr catalyst.

18. A process according to claim 9, wherein the hydrogenation in the step (d) is conducted with a Pd catalyst or a Cu—Cr catalyst.

19. The process according to claim 1, wherein steps (a)–(d) in the process are carried out sequentially.

20. A process according to claim 1, wherein the process is carried out as a batch or a continuous method.

21. The process of claim 1, wherein said Burmah catalyst is a catalyst of the following formula:

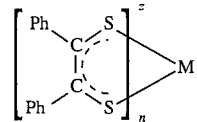

wherein M is Ni, Pd or Fe (II); Ph is a phenyl group optionally substituted with at least one substituent; n is an integer of 1, 2 or 3; z is a formal charge of the complex, selected from 0, −1 and −2.

22. The process of claim 1, wherein subsequent to the step (d) hydrogenation reaction, cymenes in said solution are recycled in said process.

* * * * *